United States Patent [19]

Elenteny

[11] Patent Number: 4,696,065
[45] Date of Patent: Sep. 29, 1987

[54] PEEL AWAY MULTI-LAYER GLOVES

[76] Inventor: Barbara Elenteny, 8140 Surrey La., Oakland, Calif. 94605

[21] Appl. No.: 25,518

[22] Filed: Mar. 13, 1987

[51] Int. Cl.⁴ .......................................... A41D 19/00
[52] U.S. Cl. ........................................ 2/168; 2/164; 2/169
[58] Field of Search ............... 2/168, 169, 164, 161 R, 2/159, 158, 243 R, 167

[56] References Cited

U.S. PATENT DOCUMENTS

| | | | |
|---|---|---|---|
| 3,110,035 | 11/1963 | La Hue | 2/168 |
| 3,633,216 | 1/1972 | Schonholtz | 2/168 |
| 3,813,695 | 6/1974 | Podell, Jr. et al. | 2/168 |
| 4,061,709 | 12/1977 | Miller et al. | 2/168 |
| 4,218,779 | 8/1980 | Hart et al. | 2/168 |
| 4,310,928 | 1/1982 | Joung | 2/168 X |
| 4,521,365 | 6/1985 | Kurtz | 2/168 X |

Primary Examiner—H. Hampton Hunter
Attorney, Agent, or Firm—Owen, Wickersham & Erickson

[57] ABSTRACT

A flexible, elastic glove for medical use has multiple layers, wherein each outermost layer is removable after use and can be discarded. The glove is formed by coating a hand mold with elastomeric material and thereafter applying a protective film including a release agent and then repeating the process to form a desired number of additional, contiguous but separable glove layers. In use, the outermost layer can be stripped away when contaminated to expose the next clean layer, so that the multi-layer glove serves to reduce the number of infections caused by cross contamination of organisms medical procedures.

8 Claims, 5 Drawing Figures

U.S. Patent    Sep. 29, 1987    Sheet 1 of 2    4,696,065
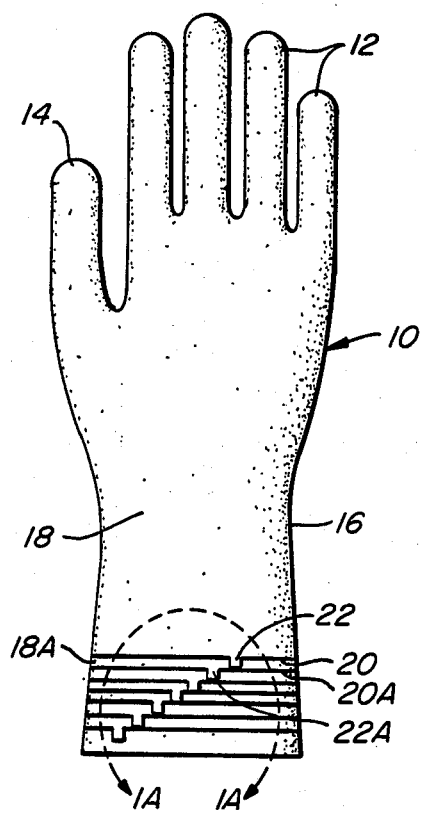
FIG._1.
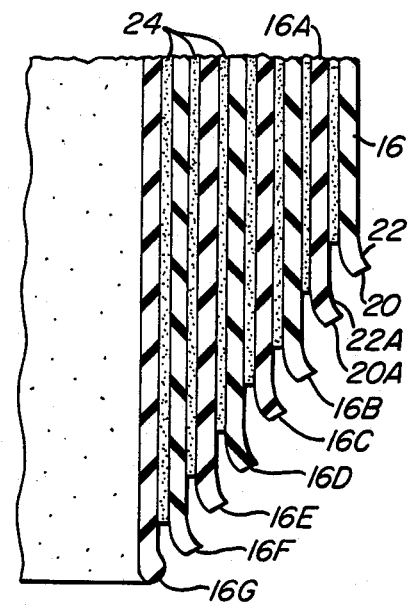
FIG._1A.
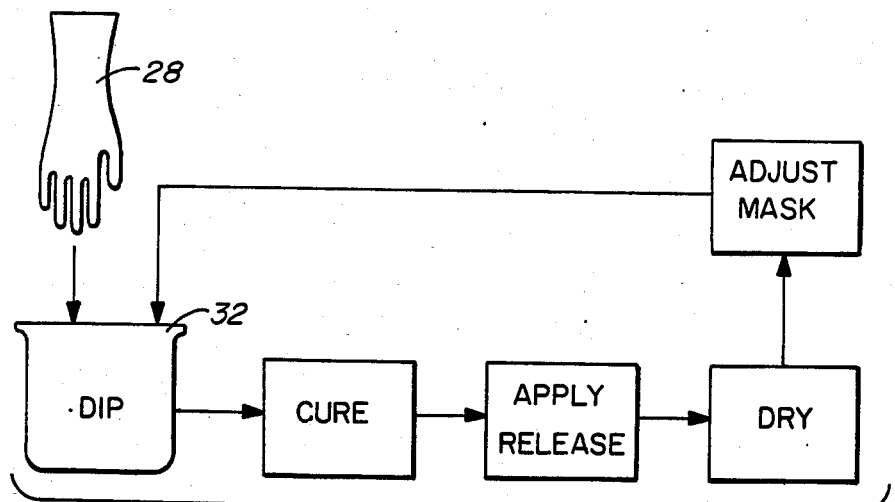
FIG._4.

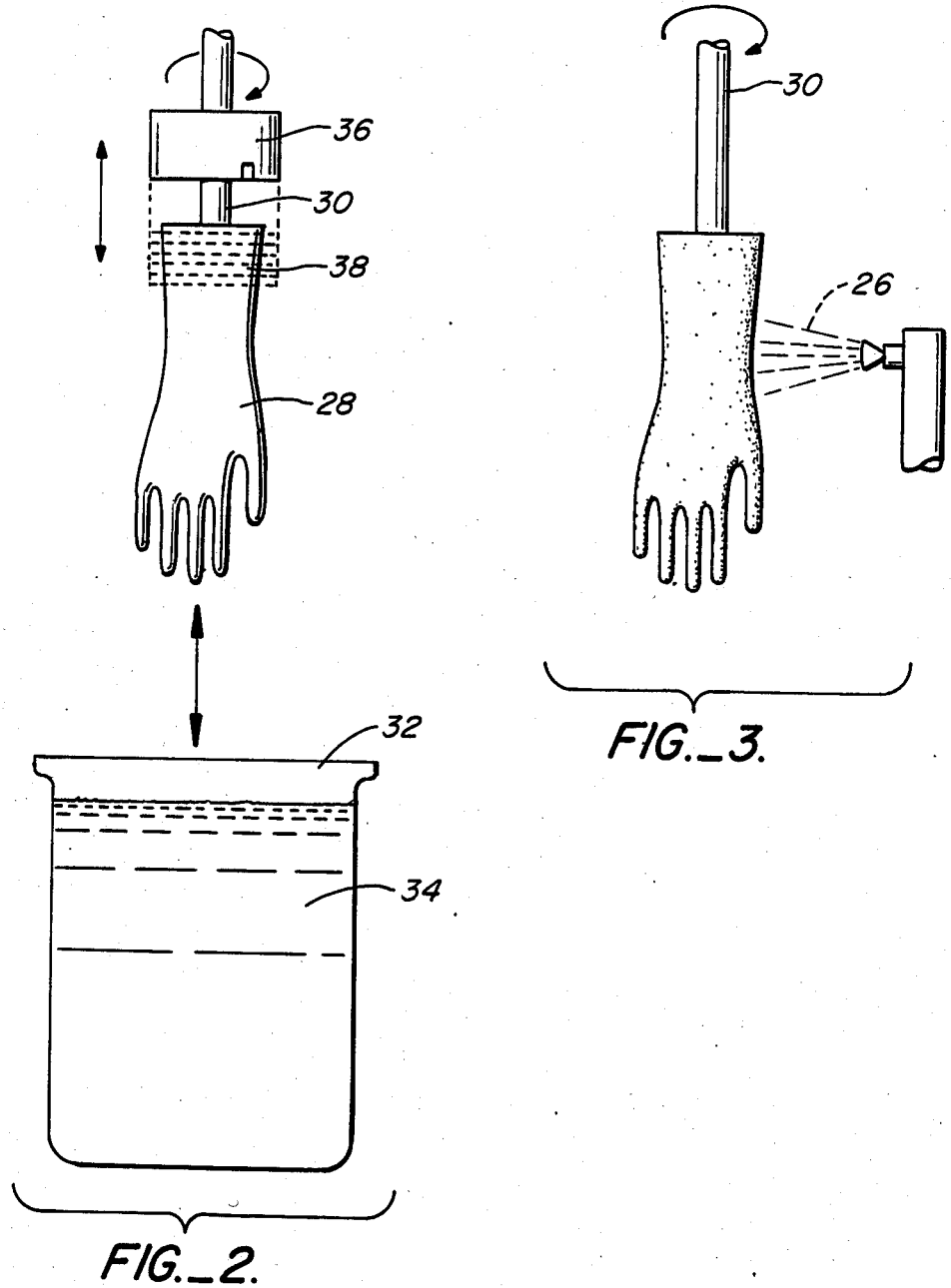

PEEL AWAY MULTI-LAYER GLOVES

BACKGROUND OF INVENTION

This invention relates to elastic gloves, and more particularly to protective elastic gloves used in medical related procedures and facilities.

BACKGROUND DESCRIPTION OF PRIOR ART

Since the 1960's health care related workers have used a simple type of elastic glove which was normally discarded after performing duties such as changing dressing, suctioning, bathing, cleaning body waste products, contact with contaminated items, and exposure to patients with known infectious diseases.

Although the Center for Disease Control (Atlanta, Ga.) recommends that sterilized gloves be used to perform these duties, health care workers have often been negligent in protecting themselves and their patients by not using gloves at the recommended times. This lack of compliance with recommendations is due to (a) lack of time to secure a clean pair of gloves (b) time required to put on a pair of gloves (c) lack of time to wash hands after removing gloves (per CDC recommendation) (d) drying effect on hands on personnel by frequent handwashing. In many medical procedures several gloves may be required for each patient and users become reluctant to spend the considerable amount of time required for pulling on and taking off gloves as they are used and discarded. It therefore became imperative for such users to find an improved method of protecting themselves and patients from dangerous organisms while saving their hands from chapping, while at the same time decreasing the time involved in putting on and removing gloves frequently.

Accordingly, a general object of the invention is to solve the aforesaid problem, and more specifically, to provide a glove which can be put on once and will not need to be replaced before carrying out a substantial number of care rendering procedures.

Another object of the invention is to provide a health care glove which will have multiple layers that can be pulled off and discarded one by one so that with each removal of an outer glove, another inner, sterilized glove is exposed and ready for use.

Another object of the invention is to provide a multi-layer elastic glove that can be used to save time and yet provide patient care in medical clinics as well as in any type of institutional procedure that requires frequent glove changes.

Still another object of my invention is to provide a method for making a multi-layer elastic glove wherein each outside layer can be readily stripped off and discarded by a user to expose a fresh, sterilized glove layer.

SUMMARY OF INVENTION

In general the invention is directed to a glove which has several disposable layers permitting general use as a disposable glove whose layers may be discarded after simple use as recommended as acceptable safe medical practice.

A glove in accordance with the preferred form of the invention is a neuter glove, in that the same glove shape is used for both hands. The glove is formed of very thin elastomeric material such as latex rubber or the like and has a wall thickness of less than 0.007 inches. The gloves may be made in layer packages of 3 to 5 for use when a delicate sense of feel is required or in 6 to 10 layers when the sense of delicate feel is not as important or when more layers are needed for frequent glove changes.

The glove is preferably formed by dipping a neuter type glove mold in latex rubber, in an uncured state, to form a coating of latex rubber having a uniform thickness of less than 0.007 inches. The mold form remains over the bath for a time to allow excess material to drip off and return to the bath. Sufficient heat is applied to cure the coating on the mold. The coated mold is then dipped into a barrier film or a mold release agent is sprayed on and allowed to dry. The mold is then redipped in the latex bath for a second layer glove. The process continues until the desired number of layers are reached.

Other objects, advantages and features of the present invention will become apparent from the following detailed description of one embodiment, presented in conjunction with the accompanying drawing.

BRIEF DESCRIPTION OF DRAWING

FIG. 1 is a view in perspective of a multi-layer glove embodying principles of the present invention.

FIG. 1A is an enlarged fragmentary view in section showing a cross-section 1A—1A of the glove in FIG. 1.

FIG. 2 is a diagrammatic view in elevation showing a glove form as it is being used to form an elastomeric layer thereon.

FIG. 3 is a diagrammatic view showing the application of a release agent to an elastomeric layer on a glove form.

FIG. 4 is flow diagram illustrating the sequence of events in a method for forming a multi-layer glove according to the present invention.

DETAILED DESCRIPTION OF EMBODIMENT

With reference to the drawing, FIG. 1 shows a single multi-layer glove 10 as it appears when ready to be worn on either the hand of a user. In general, the glove has a typical five finger neuter configuration with finger portions 12 and a thumb portion 14 of different length to approximate the size and configuration of a human hand. The glove can, of course be made in different sizes, if desired.

As shown, in a wrist area of the glove 10, an outer layer 16 has a relatively short wrist portion 18 that terminates along an edge 20. A tab 22 is provided at a preselected location along the edge 20 to provide a convenient gripping means for removing the outer layer 16 after it has been used.

A second layer 16A under the outer layer 16 has a somewhat longer wrist portion 18A having an edge 20A that extends a short distance (e.g. 0.25 inches) beyond the edge 20 of the outer layer. A removal tab 22A is provided along the edge 20A similar to but preferably offset from the tab 22 of the outer layer.

Additional, successive layers are provided on the glove 10 under the layers 16 and 16A, each layer having the same shape but a wrist portion whose length is greater than the adjacent layer covering it. In the embodiment shown, the glove has 7 inner layers in addition to the outer layer 18 which are designated 16A to 16G. However, it should be understood that, depending on the use intended for the glove 10, it may be formed with various numbers of layers and with the general configuration shown in FIG. 1.

As shown in the cross-sectional view of FIG. 1A, the successive layers 16 of the glove 10 are directly in contact with each other but with thin layers 24 of a suitable release agent between each pair of adjacent layers. Various release agents may be used, such as FFIH Product by axel, TIOLONX20 by Tiodize Corp., 20 Release Coating by Dow Corning, or Flip-A-Way anti-blocking by Ram Corp. Thus, in use, when an outer glove layer 16 is removed, it easily separates from the adjacent layer underneath to expose the fresh, sterilized layer ready for use.

A method and apparatus for making the glove 10, according to the invention, will now be described with reference to FIGS. 2-4. In FIG. 2 a hand form 28 having the desired configuration is provided on a mandrel 30 which is suspended above a container 32 of molten elastomeric material 34. Such material may be of any suitable rubber like formulation capable of producing the thin, elastomeric layers 16, 16A, etc. and well known to those skilled in the art. A band type mask 36 is provided around the wrist portion 38 of the form 28 which thus defines the outer edge 20 of the layer produced on the form. After the form has been coated with a suitable release agent, it is lowered into the container 32 of liquid or molten elastomeric material 34, so that the level thereof is above the lower edge of the band mask 36. Following a short period of time within the molten material, the form 28 is withdrawn upwardly and is allowed to dry, a process that may take only a matter of seconds. Thus, the innermost layer 16G for the glove 10 has been established on the form.

After drying, the band mask 36 is lowered over the layer 16G just formed on the wrist portion of the form 28 by a predetermined amount, (e.g. 0.25 inches) and the mask is rotated slightly so as to offset the tab 22 to be formed on the next layer. The hand form with innermost layer 16G on it is now coated, as by spraying with a layer of the release agent 26 of one of the types previously described.

Now, the form 28 with the innermost layer 16G thereon is again dipped into the container 32 of molten elastomeric material. Thereafter the drying, mask-adjusting and release coating steps are repeated to add the next layer 16E and then further succeeding layers 16D-16 as desired. The general sequence of steps for forming each layer 16 is readily depicted in the diagram of FIG. 4. As shown, the steps as described include: dipping the form, curing the layer, applying the release agent, drying, adjusting the mask, and then repeating the previous steps to form the next layer.

When the desired number of layers on the glove 10 is achieved, the multi-layer glove is stripped from the mold 28 using air jets, brushes or any other suitable means (not shown). Thereafter, a drying and friction reducing powder may be inserted into the innermost glove layer to insure comfort of use and ease of putting on the glove. In use, the wearer can perform whatever functions are necessary with the glove and thereafter, when it becomes necessary to establish a new level of sterility with a new patient or a different procedure, the outermost glove layer can be grasped by a removal tab 22 and quickly stripped away to expose the next, clean glove layer.

To those skilled in the art to which this invention relates, many changes in construction and widely differing embodiments and applications of the invention will suggest themselves without departing from the spirit and scope of the invention. The disclosures and the descriptions herein are purely illustrative and are not intended to be in any sense limiting.

What is claimed is:

1. A glove adapted to be worn on a human hand and adapted for use in medical procedures subject to bacterial contamination, said glove comprising:
   an inner layer of impervious elastomeric material;
   an outer layer of impervious elastomeric material covering said inner layer; and a plurality of additional layers of elastomeric material between said inner and outer layers, each adjacent pair of layers being separated by said release means; and
   release means between said layers for enabling a wearer of the glove to remove and strip away said outer layer whenever it becomes contaminated so that a clean inner layer will be exposed;
   said inner layer and each successive adjacent layer having a longer wrist portion than the next outermost layer, so that all multiple layers of said glove have a different length and are easily distinguishable from each other.

2. The glove as described in claim 1 wherein said release means comprises a thin coating of a mold release agent forming a substantially uniform layer between adjacent said elastomeric layers.

3. The glove as described in claim 1 wherein said inner layer has a slightly longer wrist portion than said outer layer, so that the edge of said outer layer is clearly visible when said glove is worn.

4. The glove as described in claim 1 including tab means on said outer layer for enabling a wearer to easily grasp the outermost layer for removal.

5. The glove as described in claim 1 including a visually distinguishable tab means on the outer edge of each said glove layer.

6. A method for making a multi-layered medical glove comprising the steps of:
   (1) providing hand-shaped mold;
   (2) dipping said mold into a body of liquid elastomeric material;
   (3) withdrawing said mold when a first layer of said elastomeric material has become adhered to it;
   (4) drying said first layer of elastomeric material on said mold;
   (5) applying a release agent to said first layer on said mold;
   (6) dipping said mold with said first layer into said elastomeric material and repeating steps 2-4 for as many layers as desired for said glove; and removing said glove from said mold, each successive dipping forming a layer that is shorter than the layer directly under it.

7. The method as described in claim 6 wherein said release agent is sprayed on said mold after the drying of each layer of elastomeric material has been applied.

8. The method as described in claim 6 including the steps of:
   (7) providing a band mask around a wrist portion of said mold before it is first dipped into said elastomeric material; and
   (8) lowering said band mask on said wrist portion of said mold before each subsequent dipping of said mold to form said shortened layer.

* * * * *